United States Patent [19]
Roh et al.

[11] Patent Number: 6,075,163
[45] Date of Patent: Jun. 13, 2000

[54] PROCESS FOR MANUFACTURING TEREPHTHALIC ACID

[75] Inventors: Hang-Duk Roh, Kyungki-do; Dongmok Bae, Seoul, both of Rep. of Korea

[73] Assignee: Sunkyong Industries Co., Ltd., Rep. of Korea

[21] Appl. No.: 09/101,001

[22] PCT Filed: Dec. 30, 1995

[86] PCT No.: PCT/KR95/00185

§ 371 Date: Jun. 29, 1998

§ 102(e) Date: Jun. 29, 1998

[87] PCT Pub. No.: WO97/24310

PCT Pub. Date: Jul. 10, 1997

[51] Int. Cl.$^7$ .............................. C07C 51/00; C07C 51/42
[52] U.S. Cl. ...................... 562/483; 562/486; 422/184.1
[58] Field of Search .................... 562/483, 486; 422/184.1

[56] References Cited

U.S. PATENT DOCUMENTS

| | | | |
|---|---|---|---|
| 3,120,561 | 2/1964 | Chambret | 260/515 |
| 3,544,622 | 12/1970 | England | 260/515 |
| 3,884,850 | 5/1975 | Ostrowski | 260/2.3 |
| 3,952,053 | 4/1976 | Brown, Jr. et al. | 260/525 |
| 4,355,175 | 10/1982 | Pusztaszeri | 562/483 |
| 4,542,239 | 9/1985 | Lamparter et al. | 562/487 |
| 4,578,502 | 3/1986 | Cudmore | 560/790 |
| 5,395,858 | 3/1995 | Schwartz et al. | 521/48 |

FOREIGN PATENT DOCUMENTS

| | | |
|---|---|---|
| 497662 | 1/1992 | European Pat. Off. . |
| 597751 | 10/1993 | European Pat. Off. . |
| 2123403 | 2/1984 | United Kingdom . |

OTHER PUBLICATIONS

Japanese Patent Unexamined Publication No. 03–16328, dated Jan. 24, 1991.

*Primary Examiner*—Porfirio Nazario-Gonzalez
*Attorney, Agent, or Firm*—Finnegan, Henderson, Farabow, Garrett & Dunner

[57] ABSTRACT

This invention relates to a process for manufacturing terephthalic acid and more particularly, to a process for manufacturing terephthalic acid in a high recovery rate with high purity in accordance with the practice of this invention comprising the following procedures: polyethylene terephthalate (hereinafter referred to as "PET") scrap is hydrolyzed with alkaline aqueous solution to give the slurry of terephthalic acid alkali metal/earth metal salt, then the particles of terephthalic acid formed from acid-neutralization are enlarged to recover terephthalic acid with high purity.

14 Claims, 1 Drawing Sheet

PROCESS FOR MANUFACTURING TEREPHTHALIC ACID

BACKGROUND OF THE INVENTION

Field of the Invention

This invention relates to a process for manufacturing terephthalic acid and more particularly, to a process for manufacturing the highly purified terephthalic acid in a high recovery rate, in accordance with the practice of this invention comprising the following procedures: polyethylene terephthalate (hereinafter referred to as "PET") scrap is hydrolyzed with an akaline aqueous solution to give the slurry of terephthalic acid alkali metal/earth metal salt, then the particle of terephthalic acid formed from acid-neutralization is enlarged to recover the highly purified terephthalic acid.

The PET waste scrap materials, which are discharged after using them from the end-users, refer to polyester scrap textiles, PET scrap bottles, PET scrap containers, polyethylene terephthalate scrap chips generated in the polymerization process of PET, or polyester scrap yarns generated from the process of manufacturing polyester fibers yarns and textiles. The need for the reutilization of the PET scrap, being incessantly discharged by one's daily life or in the manufacturing process, has created a great issue in the viewpoint of reducing production costs and abating environmental problems. Recently, various processes have been proposed for the recovery of terephthalic acid from the PET scrap but they arenot efficient and economical.

The conventional processes of manufacturing and recovering terephthalic acid are as follows, using the PET scrap:

In U.S. Pat. Nos. 3,120,561 and 4,578,502, PET was hydrolyzed at high temperature and pressure, cooled rapidly and crystallized to recover the precipitated terephthalic acid.

In U.S. Pat. No. 3,884,850, bis(hydroxyethyl) terephthalate was employed as a solvent to recover terephthalic acid from PET.

In U.K Pat. No. 2,123,403 and Japanese Patent Unexamined Publication No. 3-16,328, PET was hydrolyzed with a solvent such as water in the presence of decoloring carbon at 200 to 300° C., then cooled under reduced pressure to recover terephthalic acid.

In U.S. Pat. No. 3,952,053, two methods related the recovery of terephthalic acid from PET as follows: a) through the hydrolysis with sulfuric acid, the obtained mixing solution consisting of terephthalic acid and sulfuric acid was precipitated by water to recover terephthalic acid, or b) PET was placed in an aqueous solution of sodium hydroxide to precipitate unsoluble materials for removal and sulfuric acid was added to precipitate terephthalic acid. Then, ethylene glycol was extracted with organic solvent and distilled after the recovery of terephthalic acid.

In U.S. Pat. No. 4,355,175, PET was hydrolyzed by acid, diluted with cold water and filtered immediately. The resulting solution was dissolved in alkali hydroxide solution to precipitate impurities for removal and added with sulfuric acid to precipitate terephthalic acid. Then, the solution was filtered, washed with water and dried to recover terephthalic acid.

In U.S. Pat. No. 3,544,622, PET was reacted by saponification with sodium hydroxide solution at 150° C. in the presence of ethylene glycol, to prepare disodium terephthalate. Then, the resulting solution was filtered, washed with ethylene glycol or aqueous solution of disodium terephthalate at over 90° C. and dissolved in water. Activated charcoal was added to the solution at 90° C., agitated and neutralized with sulfuric acid. Then, terephthalic acid was filtered and washed with water to recover terephthalic acid.

In European Patent No. 497,662, PET was reacted with alkali metal/earth metal hydroxide at atmospheric pressure and 140 to 180° C., to prepare terephthalic acid alkali metal/earth metal salt. This material was dissolved in water to extract impurities with $C_3$ to $C_8$, alcohols, then neutralized with acid and followed by filtration to recover terephthalic acid.

In European Patent No. 597,751, PET was reacted with sodium hydroxide in the presence of a mixing extruder without the addition of solvent and then, the obtained disodium terephthalate was dissolved in water, passed through activated charcoal and neutralized with sulfuric acid. The resulting solution was filtered and washed to recover terephthalic acid.

In U.S. Pat. No. 5,395,858, PET dissolved in sodium hydroxide solution was heated to prepare both disodium terephthalate and ethylene glycol. These materials, so obtained, were heated up higher than boiling point of ethylene glycol to evaporate the solution. The remaining disodium terephthalate was dissolved in water and neutralized with acid to recover terephthalic acid.

These reported methods as aforementioned have also several problems as follows; a) a majority of their reactions was conducted at high temperature and pressure, b) they failed to illustrate some methods of removing impurities and monitoring purity, and c) even in case of monitoring said purity, the purity of terephthalic acid was not analyzed by appropriate methods for the quality measurements. In addition, in a process of filtering terephthalic acid as a final recovery step, the particle size of terephthalic acid should be sufficiently enlarged because small particles of terephthalic acid cause insufficient separation into solids and liquids which is responsible for reduction of recovery rate, and also make it difficult to perform the drying process. Nevertheless, said reported methods did not mention any steps of enlarging the particle sizes of terephthalic acid.

In this context, said reported methods are technically and economically unfavorable for commercialization and further, there are still plenty of rooms for improving environmental problems, since said reported methods failed to suggest the method of treating by-products generated in the recovery process.

BRIEF DESCRIPTION OF THE DRAWINGS

The drawing is a schematic diagram showing the process of manufacturing terephthalic acid in accordance with this invention.

SUMMARY OF THE INVENTION

Figure 1:
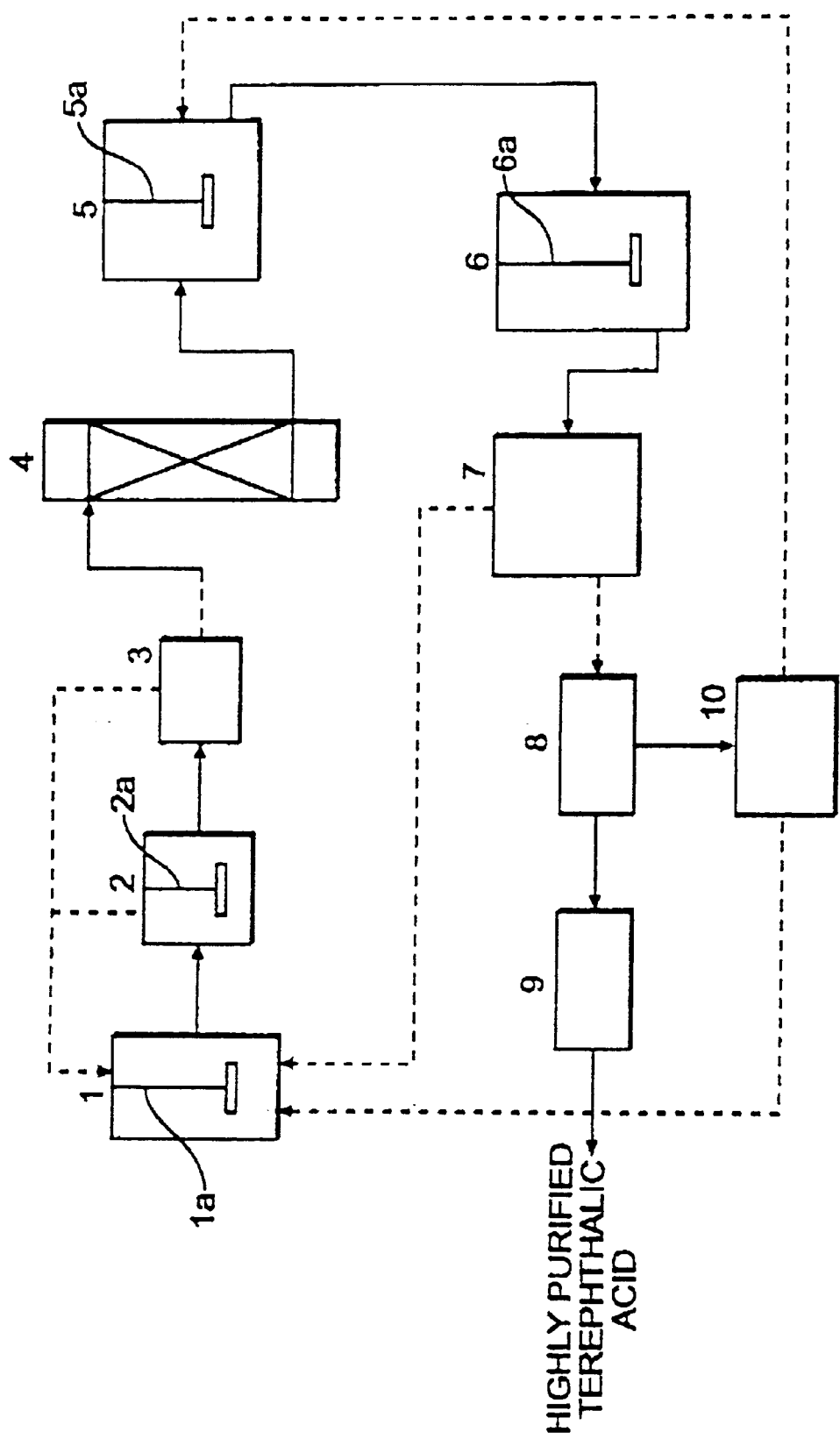

Therefore, the object of present invention is to provide a process for manufacturing terephthalic acid in accordance with the practice of this invention comprising the following procedures: PET was hydrolyzed with an alkali aqueous solution containing a wetting agent, and terephthalic acid was prepared by the neutralization of acid. Through a process of enlarging the particle of terephthalic acid in technically mild condition and with an easier method, the highly purified terephthalic acid may be yielded and in addition to that, the solvents and reaction substances discharged during the reaction process may be fed back for reuse, thus reducing the production costs of terephthalic acid.

DETAILED DESCRIPTION OF THIS INVENTION

The present invention may be described in more detail as shown below.

The present invention is characterized by a process for manufacturing terephthalic acid comprising the following steps:

(a) a process in which PET scrap is hydrolyzed by alkali metal/earth metal hydroxide in the presence of solvent such as water with a wetting agent, to prepare terephthalic acid alkali metal/earth metal salt;

(b) a process in which an aqueous solution of terephthalic acid alkali metal/earth metal salt dissolved in water was separated into solids and liquids; the solids are fed back to said (a) hydrolysis process or discharged, while the liquids are transferred to the next adsorption process;

(c) a process in which an aqueous solution of terephthalic acid alkali metal/earth metal salt is adsorbed and neutralized with add to give terephthalic acid;

(d) a crystallization process to enlarge the particle of terephthalic acid;

(e) and, a process in which the enlarged particle of terephthalic add is cooled under reduced pressure, filtered and dried.

The present invention also relates to several kinds of successively installed tanks for manufacturing terephthalic acid from PET scrap, a raw material, which is characterized by the following systems: hydrolysis system (1) where said PET scrap is hydrolyzed to prepare terephthalic acid alkali metal/earth metal salt; dissolving system (2) where terephthalic acid alkali metal/earth metal salt is dissolved; centrifuge (3); adsorption tower (4); neutralization system(5) where terephthalic acid alkali metal/earth metal salt is neutralized with add to prepare terephthalic acid; crystallization system (6) where the particle of terephthalic acid is enlarged; cooling system (7); filtering system (8) where the enlarged particle of terephthalic acid is filtered; drying system (9) where filtered terephthalic acid is dried.

The present invention is described in more detail as set forth hereunder.

According to the present invention, PET scrap is hydrolyzed with an alkali aqueous solution to prepare the slurry of terephthalic acid alkali metal/earth metal salt. Then, the resulting solution is dissolved in water, and impurities are removed during adsorption. The solution was neutralized with acid to prepare terephthalic acid and prior to the recovery of terephthalic acid, the particle of terephthalic acid is sufficiently enlarged so as to enhance the recovery rate of terephthalic add.

The process of manufacturing terephthalic acid according to this invention is referred in more detail to the drawings as follows:

Water as a solvent, PET scrap (I to 25 weight %), alkali metal/earth metal hydroxide (5 to 30 weight %) and a wetting agent (1 to 30 weight %) are charged into reaction tank (1), then agitated by agitator (1a), at reaction pressure of 1 to 20 kg/cm$^2$ and 30 to 200° C. to conduct the hydrolysis reaction at the agitation rate of 60 to 300 rpm for 30 to 120 mins. During said hydrolysis reaction, in order to enlarge the reaction surface area of PET scrap, PET scrap is cut into small particles and pulverized in less than 1 cm$^3$ and then, charged into a reaction tank(1). Hence, if less than 1 weight % of charged PET scrap in reaction tank (1) is contained in a total volume of reactants, there is no economic feasibility and in case of exceeding 25 weight %, a higher concentration of terephthalic acid salt makes it more difficult to operate the reaction in an efficient manner. And alkali metal/earth metal hydroxide used in this invention refers to alkali metal hydroxide or alkali earth metal hydroxide. From said hydrolysis reaction, if less than 5 weight % of alkali metal/earth metal hydroxide is contained in the total volume of reactants, the conversion yield in reaction is low and in case of exceeding 30 weight %, there is no economic feasibility due to the increased production cost and recycle of intermediate and by-products to be inevitably generated. And according to this invention, a wetting agent may be selected from the group containing alcohols of $C_1$ to $C_4$ and surfactant. If less than 1 weight % of said wetting agent is contained in the total volume of reactants, the reaction rate become low and in the case of exceeding 30 weight %, the relative decrease of water content may enhance the concentration of terephthalic acid alkali metal/earth metal salt and thus, the increased viscosity makes it difficult to operate the reaction in an efficient manner. In addition, if the reaction temperature in said hydrolysis is less than 30° C. or reaction pressure is less than 1 kg/cm$^2$, the reaction rate becomes very low and this proved to be economically infeasible.

In contrast, if the temperature in said hydrolysis reaction exceeds 200° C. or reaction pressure also exceed 20 kg/cm$^2$, further hike in facility investment costs to maintain high reaction temperature and pressure including energy cost thereto will also make the process economically infeasible. After said hydrolysis reaction, PET is converted to terephthalic acid alkali metal/earth metal salt. Now that the solubility of terephthalic acid alkali metal/earth metal salt to water is about 13 weight % at room temperature, so it may exist in the form of slurry.

The solution of terephthalic acid alkali metal/earth metal salt is transferred from reaction tank (1) to dissolving tank (2). Said solution is added with water and agitated constantly by agitator (2a) at 60 to 300 rpm for 10 to 60 mins, at atmospheric pressure and 20 to 100° C. to prepare an aqueous solution of terephthalic acid alkali metal/earth metal salt. Hence, 0.5 to 3.0 times of water in weight is used in proportion to the slurry of terephthalic and alkali metal/earth metal salt. If water is used in less than 0.5 times in weight, terephthalic acid alkali metal/earth metal salt is not freely soluble in water and even if freely soluble, the viscosity of said solution is very high so that the next adsorption process may not be operated in an efficient manner, while in the case of exceeding 3.0 times in weight, the sizes of both dissolving tank and adsorption tower should be large in proportion to gradual increase of water in use. Thus, additional facility investment cost including operation cost for reaction thereto should be inevitable. The reaction in dissolving tank (2) is preferably conducted at atmospheric pressure and 20 to 100° C. In order to ensure better adsorption efficiency in the next adsorption process, the dissolving condition exceeding 100° C. is not preferable. In addition, the evaporated alcohol and water in the process of solubility is condensed and fed back to reaction tank (1).

An aqueous solution of terephthalic acid alkali metal/earth metal salt, passed through dissolving tank (2), is also separated solids and liquids by centrifuge (3); the solids containing non-reactants and unsoluble substances are fed back to reaction tank (1) or discharged, while the liquids are delivered to adsorption tower (4).

Adsorption tower (4) plays a role of removing impurities contained in PET (e.g., metal, metal compound, organic compound, dirt, etc.). The purity of terephthalic acid, a final product, is determined based upon the removal efficiency in adsorption tower (4). According to this invention, activated carbon as a filling material of adsorption tower (4), which is stable in alkali solution, is selected for use and in consideration of its adsorption rate, the surface area of activated carbon per unit volume should be preferably within 500 to 1,500 m$^2$/g. The reaction of adsorption tower (4) should be preferably conducted at reaction pressure of 0.01 to 10.0 kg/cm$^2$ and 20 to 100° C., so as to further enhance the efficiency of removing impurities. The appropriate residence time in adsorption tower (4) is 1 to 60 mins but the residence time may be more or less adjusted in accordance with the reaction pressure.

The aqueous solution of terephthalic acid alkali metal/earth metal salt, passed through adsorption tower (4), is transferred to neutralization tank (5) for neutralization with acid. While agitating by agitator (5a) in neutralization tank (5), said solution is mixed slowly with such strong acid as hydrochloric acid, sulfuric acid, nitric acid and phosphoric acid. Then, terephthalic acid alkali metal/earth metal salt is neutralized to prepare terephthalic acid and alkali metal/earth metal salt individually. During the neutralization reaction, two equivalence points are formed; the 1st equivalence point is detected when the pH of said solution is between 9.0 and 6.0, where alkali metal/earth metal hydroxide is neutralized with acid to prepare alkali metal/earth metal salt, and the 2nd equivalence point is detected when the pH of said solution is between 4.0 and 2.0, where terephthalic acid alkali metal/earth metal salt is neutralized by add to prepare terephthalic add. During said neutralization reaction, therefore, acid should be incessantly provided until the pH of said solution becomes 4.0 to 2.0.

After said neutralization reaction, the obtained alkali metal/earth metal salt is freely soluble in water due to its larger solubility to water, while terephthalic acid in solid state is crystallized. Since the particle size of crystallized terephthalic acid is so small, terephthalic acid may not be efficiently separated by a method of separating solids and liquids (e.g., centrifugation or filtration). Even if separated, its recovery rate is quite low and thus, the commercial application is not economically feasible. According to this invention, therefore, the slurry of terephthalic acid, so obtained from said neutralization process, is charged into crystallization tank (6) to sufficiently enlarge the particles size of terephthalic acid. One to five crystallization tanks (6) in series is/are connected and each crystallization tank (6) is operated in such a manner that temperature may be lowered stepwise. With said system, the particle size may be enlarged stepwise, thus making it possible to decrease the small particles. Crystallization temperature drop in tank (6) should be preferably within 30 to 50° C.

All the crystallization tanks (6) should be operatable within the following specification : temperature in 120 to 300° C., pressure in 2 to 86 kg/cm$^2$ and agitation rate at 60 to 300 rpm. The total residence time required to completely pass through crystallization tank (6) is preferably 30 to 180 mins. In addition, since the process of terephthalic acid crystallization is conducted at high temperature and pressure, excess acid may cause corrosion of crystallization tank (6). In this connection, any acid contained in the slurry of terephthalic acid, passed through said neutralization process, should be lower than 10 weight %. Strong corrosion-resistant material should be selected such as stainless steel type 316 or titanium for crystallization tank The sufficiently enlarged terephthalic acid in said crystallization tank (6) is charged into the next cooling tank (7) and cooled at pressure of 0.1 to 1.0 kg/cm$^2$ and temperature of 60 to 90° C. Hence, alcohol contained in the slurry is evaporated with water.

The evaporated alcohol and water are condensed and then, fed back to reaction tank (1).

The slurry of cooled terephthalic acid is delivered to filter (8) to separate solids and liquids. The operation temperature of filter (8) depends on the slurry temperature of terephthalic acid and the temperature is preferably maintained at 60 to 80° C. The pressure should be preferably 0.1 to 0.8 kg/cm$^2$. Based upon said method of separating solids and liquids, terephthalic acid is separated as wet cake and alkali metal/earth metal as filtrate solution. The filtered terephthalic acid is washed with water and in consideration of washing efficiency 0.5 to 1.2 times of water to terephthalic acid (30 to 80° C.) in proportion to terephthalic acid is preferably used.

The filtered terephthalic acid is charged into dryer (9) and dried at pressure of 0.5 to 1.0 kg/cm$^2$ and 100 to 150° C. for 10 to 120 mins, to give terephthalic acid, a final product of this invention.

In addition, the filtrate discharged from said filtration process is concentrated by evaporating water, or without evaporation of water, the filtrate is charged into electrodialyzer (10) using bipolar membrane, to individually separate acid and base of alkali metal/earth metal hydroxide. The acid, so separated and recovered, is fed back to neutralization tank (5), while alkali metal hydroxide/earth metal is also fed back to reaction tank (1).

In a more detailed manner, alkali metal/earth metal salt (e.g., sodium hydrochloride or sodium sulfate) contained in said filtrate is electrolyzed. Then, alkali metal/earth metal ion such as Na$^+$ ion, passed through cation membrane, is bound with OH$^-$ ion to form alkali metal/earth metal hydroxide such as sodium hydroxide. In addition, the acidic anion such as Cl$^-$ ion or SO$_4^{2-}$ ion, passed through anion membrane, is bound with H$^+$ ion to form acids such as hydrochloric acid or sulfuric acid.

As described in the above, this invention is intended to provide a process for reusing the feed-back reacting raw materials including solvents discharged from each manufacturing step, thus making it possible to reduce product costs and also to abate environmental problems caused by waste materials. Further, terephthalic acid, so separated and recovered from said manufacturing process, may be obtained with a high yield of 98% or better. This invention is explained in more detail by the following examples, but the claims are not limited to these examples.

EXAMPLE 1

500 g of water and 30 g of sodium hydroxide were charged into reaction tank (1) and dissolved. After the addition of 200 g of methanol and 10 g of pulverized PET scrap, the mixture was agitated by agitator (300 rpm) at pressure of 8 kg/cm$^2$ and temperature of 150° C. for 120 mins.

The reaction solution in reaction tank (1) was transferred to dissolving tank (2), added with 400 g of water and agitated by agitator (2a, 60 rpm) at atmospheric pressure and temperature of 65° C. for 10 mins An aqueous solution of terephthalic acid alkali metal/earth metal salt, passed through dissolving tank (2), was under centrifuge (3) to individually separate solids and liquids.

The solids-were fed back to reaction tank (1). 0.14 g of unreacting PET was contained in said solids and thus, it is well understood that the reaction rate of PET was 98.6%.

The liquids, passed through centrifuge (3), were transferred to adsorption tower (4) and adsorbed at reaction pressure of 0.01 kg/cm$^2$ and temperature of 30° C. for 1 min. The adsorption tower (4) was filled with activated charcoal of surface area of 1,500 m$^2$/g.

An aqueous solution of terephthalic acid alkali metal/ earth metal salt, passed through adsorption tower (4), was transferred to neutralization tank (5). Then, the solution was agitated by agitator (5a) in neutralization tank and added slowly with hydrochloric acid and incessantly until the pH of solution was 2.0. As a result of monitoring by SEM, the particle of terephthalic acid formed from said neutralization process, its particle size (5 to 20 μM) was very small.

Said neutralization solution was charged into crystallization tank (6) to enlarge the particle size of terephthalic acid. The crystallization tank. (6) is of stainless steel type 316 and has the following reaction requirements: temperature in 150° C., pressure in 5 kg/cm$^2$ and agitation rate at 60 rpm.

The sufficiently enlarged slurry of terephthalic acid in said crystallization tank (6) was charged into the next cooling tank (7) and cooled under reduced pressure, at pressure of 1 kg/cm$^2$ and temperature of 90° C. Hence, the evaporated methanol and water were condensed and fed back to reaction tank (1). The cooled slurry of terephthalic acid was delivered to filter (8) to individually separate solids and liquids, at reaction pressure of 0.8 kg/cm$^2$ and temperature of 80° C. Then, terephthalic acid in solid state was recovered. The filtered terephthalic acid was charged into dryer (9) and dried at reaction pressure of 1 kg/cm$^2$ and temperature of 150° C. for 10 mins to give 8.5 g of terephthalic acid.

Further, the filtrate discharged from said filter (8) was charged into electrodialyzer (10) with 3 chamber-type bipolar membrane and sodium hydrochloride contained in said filtrate was electrolyzed to separate hydrochloric acid and sodium hydroxide. Then, each of said alkali and add was individually fed back to reaction tank (1) or neutralization tank (5).

EXAMPLE 2

110 g of water and 60 g of sodium hydroxide were charged into reaction tank (1) and dissolved. After the addition of 30 g of methanol, 1 g of surfactant (SURMAX CS 727, Chemax Inc.) and 20 g of pulverized PET scrap, the mixture was agitated by an agitator (200 rpm) at atmospheric pressure and temperature of 80° C. for 60 mins.

The reaction solution in reaction tank (1) was transferred to dissolving tank (2), added with 400 g of water and agitated by agitator (2a, 200 rpm) at atmospheric pressure and temperature of 50° C. for 30 mins.

An aqueous solution of terephthalic acid alkali metal/ earth metal salt, passed through solubility tank (2), was under centrifuge (3) to individually separate solids and liquids. The solids were fed back to reaction tank (1). 1.28 g of unreacting PET was contained in said solids and thus, it is well understood that the reaction rate of PET was 93.6%.

The liquids, passed through centrifuge (3), were transferred to adsorption tower (4) and adsorbed at pressure of 0.1 kg/cm$^2$ and temperature of 50° C. for 10 min. The adsorption tower (4) was filled with activated charcoal of surface area of 1,500 m$^2$/g.

An aqueous solution of terephthalic acid alkali metal/ earth metal salt terephthalate, passed through adsorption tower (4), was transferred to neutralization tank (5).

Then, the solution was agitated by agitator (5a) in neutralization tank and added slowly with 97% sulfuric acid and incessantly until the pH of reaction solution became 4.0. As a result of monitoring by SEM, the particle of terephthalic acid formed from said neutralization process, its particle size (5 to 10 μm) was very small.

Said neutralization solution was charged into crystallization tank (6) to enlarge the particle of terephthalic acid. The crystallization tank (6) is of stainless steel type 316 connected with two crystallization tanks in series and each of crystallization tank has the following reaction requirements: pressure in 15 to 25 kg/cm$^2$ and agitation rate at 150 rpm. In addition, the temperature of the first crystallization tank was determined at 200° C. in such a fabrication that the temperature of said crystallization tank was lowered to 50° C. stepwise and the total residence time, passed through the whole crystallization tank(6), was 60 mins.

The sufficiently enlarged slurry of terephthalic acid in said crystallization tank (6) was charged into the next cooling tank (7) and cooled under reduced pressure, at pressure of 1 kg/cm$^2$ and temperature of 90° C. Hence, the evaporated methanol and water were condensed and fed back to reaction tank (1). The slurry of cooled terephthalic add was delivered to filter (8) to individually separate solids and liquids, at pressure of 0.5 kg/cm$^2$ and temperature of 80° C. Then, terephthalic acid in wet cake was recovered. The filtered terephthalic acid was charged into dryer (9) and dried at pressure of 0.5 kg/cm$^2$ and temperature of 150° C. for 60 mins to give 16.2 g of terephthalic acid.

Further, the filtrate discharged from said filter (8) was charged into electrodialyzer (10) with 3 chamber-type bipolar membrane and sodium sulfate contained in said filtrate was electrolyzed to separate sulfuric acid and sodium hydroxide. Then, each of said alkali and acid was individually fed back to reaction tank (1) or neutralization tank (5).

EXAMPLE 3

300 g of water and 150 g of sodium hydroxide were charged into reaction tank (1) and dissolved. After the addition of 300 g of methanol, 5 g of surfactant (SURMAX CS 727, Chemax Inc.) and 250 g of pulverized PET scrap, the mixture was agitated by an agitator (100 rpm) at pressure of 5 kg/cm$^2$ and temperature of 100° C. for 120 mins.

The solution in reaction tank (1) was transferred to dissolving tank (2), added with 1,500 g of water and agitated by agitator (2a, 300 rpm) at atmospheric pressure and temperature of 50° C. for 60 mins. Hence, the evaporated alcohol and water were condensed and fed back to reaction tank (1).

An aqueous solution of terephthalic acid alkali metal/ earth metal salt, passed through dissolving tank (2), was under centrifuge (3) to individually separate solids and liquids. The solids were fed back to reaction tank (1) or discharged. 28.2 g of unreacting PET was contained in said solids and thus, it is well understood that the reaction rate of PET was 88.7%.

The liquids, passed through centrifuge (3), were transferred to adsorption tower (4) and adsorbed at pressure of 1 kg/cm$^2$ and temperature of 80° C. for 10 mins. The adsorption tower (4) was filled with activated charcoal of surface area of 1,500 m$^2$/g.

An aqueous solution of terephthalic acid alkali metal/ earth metal salt, passed through adsorption tower (4), was transferred to neutralization tank (5). Then, the solution was agitated by agitator (5a) in neutralization tank and added slowly with 97% sulfuric acid and incessantly until the pH of solution was 3.2. As a result of monitoring by SEM, the particle of terephthalic acid formed from said neutralization process, its particle size (10 μm) was very small.

Said neutralization solution was charged into crystallization tank (6) to enlarge the particle of terephthalic acid. The crystallization tank (6) is of titanium or stainless steel type 316 which was connected with five crystallization tanks in series and each of crystallization tank has the following reaction requirements: pressure in 2 to 86 kg/cm² and agitation rate at 120 to 200 rpm. In addition, the temperature of the first crystallization tank was determined at 300° C. in such a fabrication that the temperature of said crystallization tank was lowered to 30 to 5° C. stepwise and the total residence time, passed through the whole crystallization tank (6), was 180 mins.

The sufficiently enlarged slurry of terephthalic acid in said crystallization tank (6) was charged into the next cooling tank (7) and cooled under reduced pressure, at pressure of 0.1 kg/cm² and temperature of 90° C. Hence, the evaporated methanol and water were condensed and fed back to reaction tank (1). The cooled slurry of terephthalic acid was delivered to filter (8) to individually separate solids and liquids, at pressure of 0.1 kg/cm² and temperature of 80° C. Then, terephthalic acid in wet cake was recovered. The filtered terephthalic acid was charged into dryer (9) and dried at pressure of 0.7 kg/cm² and temperature of 100° C. for 180 mins to give 186.9 g of terephthalic acid.

Further, the filtrate discharged from said filter (8) was charged into electrodialyzer (10) with 3 chamber-type bipolar membrane and sodium sulfate contained in said filtrate was electrolyzed to separate sulfuric acid and sodium hydroxide. Then, each of said alkali and add was individually fed back to reaction tank (1) or neutralization tank (5).

EXAMPLE 4

735 g of water and 50 g of sodium hydroxide were charged into reaction tank (1) and dissolved.

After the addition of 100 g of methanol and 115 g of pulverized PET scrap, the mixture was agitated by an agitator (300 rpm) at pressure of 20 kg/cm² and temperature of 200° C. for 60 mins.

The solution in reaction tank (1) was transferred to dissolving tank (2), added with 1,000 g of water and agitated by agitator (2a, 300 rpm) at pressure of 1 kg/cm² and temperature of 100° C. for 20 mins. Hence, the evaporated alcohol and water were condensed and fed back to reaction tank (1).

An aqueous solution of terephthalic acid alkali metal/earth metal salt, passed through dissolving tank (2), was under centrifuge (3) to individually separate solids and liquids. The solids were fed back to reaction tank (1) or discharged. 0.16 g of unreacting PET was contained in said solids and thus, it is well understood that the reaction rate of PET was 99.7%.

The liquids, passed through centrifuge (3), were transferred to adsorption tower (4) and adsorbed at pressure of 10 kg/cm² and temperature of 100° C. for 5 mins. The adsorption tower (4) was filled with activated charcoal of surface area of 900 m²/g.

An aqueous solution of terephthalic acid alkali metal/earth metal salt, passed through adsorption tower (4), was transferred to neutralization tank (5). Then, the solution was agitated by agitator (5a) in neutralization tank and added slowly with 97% sulfuric acid and incessantly until the pH of reaction solution became 2.0. As a result of monitoring by SEM, the particle of terephthalic acid formed from said neutralization process, its particle size (10 to 20 μm) was very small.

Said neutralization solution was charged into crystallization tank (6) to enlarge the particle of terephthalic acid.

The crystallization tank (6) is of titanium or stainless steel type 316 which was connected with three crystallization tanks in series and each of crystallization tank has the following reaction requirements: pressure in 2 to 15 kg/cm² and agitation rate in 200 to 300 rpm. In addition, the temperature of the first crystallization tank was determined at 200° C. in such a fabrication that the temperature of said crystallization tank was lowered to 30 to 50° C. stepwise and the total residence time, passed through the whole crystallization tank (6), was 60 mins.

The sufficiently enlarged terephthalic acid slurry in said crystallization tank (6) was charged into the next cooling tank (7) and cooled under reduced pressure, at pressure of 0.1 kg/cm² and temperature of 90° C. Hence, the evaporated methanol and water were condensed and fed back to reaction tank (1). The slurry of cooled terephthalic acid was delivered to filter (8) to individually separate solids and liquids, at pressure of 0.1 kg/cm² and temperature of 80° C. Then, terephthalic acid in wet cake was recovered. The filtered terephthalic acid was charged into dryer (9) and dried at pressure of 0.8 kg/cm² and temperature of 120° C. for 120 mins to give 99 g of terephthalic acid.

Further, the filtrate discharged from said filter (8) was charged into electrodialyzer (10) with 3 chamber-type bipolar membrane and sodium sulfate contained in said filtrate was electrolyzed to separate sulfuric acid and sodium hydroxide. Then, each of said alkali and add was individually fed back to reaction tank (1) or neutralization tank (5).

EXPERIMENT

Each of terephthalic acid, so obtained from said EXAMPLE 1 to 4, was analyzed by the following methods:

(1) Purity: As for terephthalic acid, so obtained from PET, μ-bondapak C18 column was introduced to monitor the concentration of its impurities on high pressure liquid chromatography (HPLC).

(2) Average particle size: Sieve analysis method and SEM were introduced to monitor average particle size.

(3) Transmittance: With a solution prepared by dissolving terephthalic acid in an aqueous solution of potassium hydroxide, spectrometer, SPECTRONIC 601(MILTON ROY)was introduced to monitor its transmittance at 340 nm.

(4) Color value: DIANO Match Scan II Colorimeter was introduced to monitor the values of color L, a and b.

(5) Metal content: XRF (X-ray refractive fluorescence) was introduced to monitor the metal content of Co, Mn and Fe.

TABLE

| | EXAMPLE | | | |
|---|---|---|---|---|
| | 1 | 2 | 3 | 4 |
| Recovery rate (%) | 98.6 | 93.6 | 86.6 | 99.6 |
| Purity (%) | 98.5 | 98.0 | 99.3 | 99.1 |
| Average particle size (μm) | 54 | 66 | 102 | 81 |
| Transmittance (%) | 59.8 | 70.1 | 55.4 | 73.8 |
| Color value | | | | |
| L | 97.9 | 96.6 | 97.3 | 98.4 |
| a | −0.5 | −0.5 | −0.2 | −0.3 |
| b | 1.1 | 1.7 | 2.1 | 1.1 |
| Metal content (ppm) | | | | |
| Co | 0 | 0.1 | 2.2 | 0 |
| Mn | 0 | 0 | 0.1 | 0 |
| Fe | 4.6 | 7.2 | 16.1 | 5.3 |

The results of said table show that the purity of terephthalic acid, so obtained EXAMPLE 1 to 2, was more or less low but this was owing to the fact that isophthalic acid was added in the process of manufacturing PET. The terephthalic acid containing isophthalic acid is useful in preparing polyester resin.

Therefore, now that terephthalic acid recovered by the methods of this invention does not contain any metals and also maintain a high purity, it is very useful in preparing polyester resin.

What is claimed is:

1. A process for manufacturing terephthalic acid wherein polyethylene terephthalate is hydrolyzed and crystallized to give terephthalic acid in accordance with the practice of this invention comprising the following processes:

(a) a process in which PET scrap is hydrolyzed by alkali metal/earth metal hydroxide in the presence of solvent and a wetting agent, to prepare terephthalic acid alkali metal/earth metal salt;

(b) a process in which an aqueous solution of terephthalic acid alkali metal/earth metal salt dissolved in water was separated as solids and liquids; the solids are fed back to said (a) step hydrolysis process or discharged, while the liquids are transferred to the next adsorption process;

(c) a process in which an aqueous solution of terephthalic acid alkali metal/earth metal salt is adsorbed and neutralized with acid to give terephthalic acid;

(d) a crystallization process to enlarge the particle of terephthalic acid;

(e) and, a process in which the enlarged partide of terephthalic acid is cooled under reduced pressure, filtered and dried.

2. The process for manufacturing terephthalic acid as claimed in claim 1 wherein in (a) step, polyethylene terephthalate waste scrap materials may, for use, include polyester textiles scrap, polyethylene terephthalate scrap bottles, polyethylene terephthalate scrap containers, polyethylene terephthalate scrap chips generated in the polymerization process of polyethylene terephthalate, or polyeste scrap yarns generated from the process of manufacturing polyester fiber, yarn and textile.

3. The process for manufacturing and recovering terephthalic acid as claimed in claim 1 or 2 wherein said polyethylene 1 to 25 weight % of terephthalate scrap is added in a total volume of hydrolysis.

4. The process for manufacturing terephthalic acid as claimed in claim 1 wherein 5 to 30 said weight % of alkali metal/earth metal hydroxide is contained in a total volume of hydrolysis.

5. The process for manufacturing terephthalic acid as claimed in claim 1 wherein 1 to 30 weight % of said wetting agent is contained in a total volume of hydrolysis.

6. The process for manufacturing terephthalic acid as claimed in claim 1 wherein said (a) step is conducted at pressure of 1 to 20 kg/cm$^2$ and temperature of 30 to 200° C.

7. The process for manufacturing terephthalic acid as claimed in claim 1 wherein in said (b) step, 0.5 to 3.0 times of water in weight is used in proportion to alkali metal/earth metal salt terephthalate.

8. The process for manufacturing terephthalic acid as claimed in claim 1 wherein said (d) step is conducted in the crystallization tank where one to five crystallization tanks is/are connected in series and the temperature of each crystallization tank drops stepwise 30 to 50° C.

9. The process for manufacturing terephthalic acid as claimed in claim 8 wherein said crystallization tank is kept constant at pressure of 2 to 86 kg/cm$^2$ and temperature of 120 to 300° C.

10. The process for manufacturing terephthalic acid as claimed in claim 1 wherein said (e) step is conducted at pressure of 0.1 to 1.0 kg/cm$^2$ and temperature of 60 to 96° C.

11. The process for manufacturing terephthalic acid as claimed in claim 1 wherein in (e) step, alcohol and water discharged is fed back to said (a) hydrolysis process.

12. The process for manufacturing terephthalic acid as claimed in claim 1 wherein in (e) step, the filtrate is charged into an electrodialyzer using bipolar membrane, to separate acid and alkali metal/earth metal hydroxide; the acid is fed back to said (c) step and alkali metal/earth metal hydroxide is fed back to said (a) step.

13. The process according to claim 1, wherein said solvent in step (a) comprises water.

14. A successively installed system for manufacturing terephthalic acid from polyethylene terephthalate waste scrap material, comprising: a hydrolysis system where said PET scrap is hydrolyzed to prepare terephthalic acid alkali metal/earth metal salt; a dissolving system where terephthalic acid alkali metal/earth metal salt is dissolved; a centrifuge; an adsorption tower; a neutralization system where terephthalic acid alkali metal/earth metal salt is neutralized with acid to prepare terephthalic acid; a crystallization system where the particle of terephthalic acid is enlarged; a cooling system; a filtering system where the enlarged particle of terephthalic acid is filtered; a drying system where filtered terephthalic acid is dried; and an electrodialyzer using at least one bipolar membrane.

* * * * *